United States Patent
Gunnerson et al.

(10) Patent No.: US 9,743,873 B2
(45) Date of Patent: *Aug. 29, 2017

(54) ROTATABLE DISK-SHAPED FLUID SAMPLE COLLECTION DEVICE

(71) Applicant: Ortho-Clinical Diagnostics, Inc., Raritan, NJ (US)

(72) Inventors: Kory A. Gunnerson, Cincinnati, OH (US); Raymond F. Jakubowicz, Rush, NY (US); Andrew M. Kirsch, Webster, NY (US); James Ellis Robinson, Rochester, NY (US); Daniel P. Salotto, Rochester, NY (US); David A. Tomasso, Rochester, NY (US); Zhong Ding, Pittsford, NY (US); William Franklin Gottermeier, Pittsford, NY (US); Aaron Michael Swick, Cincinnati, OH (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 115 days.

This patent is subject to a terminal disclaimer.

(21) Appl. No.: 14/208,606

(22) Filed: Mar. 13, 2014

(65) Prior Publication Data

US 2014/0275866 A1 Sep. 18, 2014

Related U.S. Application Data

(60) Provisional application No. 61/790,961, filed on Mar. 15, 2013.

(51) Int. Cl.
*G01N 33/00* (2006.01)
*A61B 5/15* (2006.01)
(Continued)

(52) U.S. Cl.
CPC ...... *A61B 5/150343* (2013.01); *A61B 5/1468* (2013.01); *A61B 5/14507* (2013.01);
(Continued)

(58) Field of Classification Search
CPC . G01N 33/49; B01L 3/502; B01L 2200/0684; A61B 5/150343
See application file for complete search history.

(56) References Cited

U.S. PATENT DOCUMENTS

| 5,120,643 A | 6/1992 | Ching et al. |
| 5,559,041 A | 9/1996 | Kang et al. |

(Continued)

FOREIGN PATENT DOCUMENTS

| WO | WO 03/103835 A1 | 12/2003 |
| WO | WO 2005/089082 A2 | 9/2005 |

(Continued)

*Primary Examiner* — Sam P Siefke
(74) *Attorney, Agent, or Firm* — Barlcay Damon, LLP

(57) ABSTRACT

A sample collection device for a fluid includes: a substantially disk-shaped body having a periphery; a capillary channel extending through the body and bounded by the periphery, having a first end and a second end, wherein the first end is adapted to draw the fluid into the channel by capillary action; a sample collection well located in the vicinity of the second end and in fluid communication with the capillary channel; and an axis of rotation extending through the center of the disk and which is substantially perpendicular to the major surface of the disk-shaped body. In a preferred embodiment, the sample collection device is adapted to rotate about the axis of rotation within a cartridge having a housing comprising an air vent in fluid communication with the capillary channel when the disk is rotated in a first position.

16 Claims, 12 Drawing Sheets

(51) Int. Cl.
  *B01L 3/00* (2006.01)
  *G01N 33/49* (2006.01)
  *A61B 5/145* (2006.01)
  *A61B 5/1468* (2006.01)
  *A61B 5/157* (2006.01)
  *A61B 10/00* (2006.01)

(52) U.S. Cl.
  CPC ........ *A61B 5/157* (2013.01); *A61B 5/150213* (2013.01); *A61B 10/007* (2013.01); *B01L 3/502* (2013.01); *G01N 33/49* (2013.01); *B01L 2200/025* (2013.01); *B01L 2200/0684* (2013.01); *B01L 2300/0681* (2013.01); *B01L 2300/087* (2013.01); *B01L 2300/161* (2013.01); *B01L 2400/0406* (2013.01); *B01L 2400/0487* (2013.01); *B01L 2400/0644* (2013.01)

(56) References Cited

U.S. PATENT DOCUMENTS

| | | |
|---|---|---|
| 5,714,389 A | 2/1998 | Charlton et al. |
| 6,139,800 A | 10/2000 | Chandler |
| 6,228,660 B1 | 5/2001 | May et al. |
| 6,372,542 B1 | 4/2002 | Martin et al. |
| 6,733,682 B1 | 5/2004 | Björkman et al. |
| 6,811,736 B1 | 11/2004 | Ohman et al. |
| 6,884,370 B2 | 4/2005 | Ohman et al. |
| 7,416,700 B2 | 8/2008 | Buechler et al. |
| 2005/0042766 A1 | 2/2005 | Ohman et al. |
| 2006/0052810 A1* | 3/2006 | Freeman .............. A61B 5/1411 606/181 |
| 2006/0239859 A1 | 10/2006 | Ohman et al. |
| 2006/0285996 A1 | 12/2006 | Ohman et al. |
| 2006/0289787 A1 | 12/2006 | Ohman et al. |
| 2007/0231883 A1 | 10/2007 | Lindstrom et al. |
| 2012/0271125 A1* | 10/2012 | Bernstein ............. A61B 5/1519 600/309 |
| 2013/0210036 A1 | 8/2013 | Kanaley et al. |
| 2014/0206098 A1 | 7/2014 | Hosimer et al. |
| 2014/0272941 A1* | 9/2014 | Gunnerson ......... B01L 3/50273 435/5 |

FOREIGN PATENT DOCUMENTS

| | | |
|---|---|---|
| WO | WO 2005/118139 A1 | 12/2005 |
| WO | WO 2006/137785 A1 | 12/2006 |
| WO | WO 2007/149042 A1 | 12/2007 |

* cited by examiner

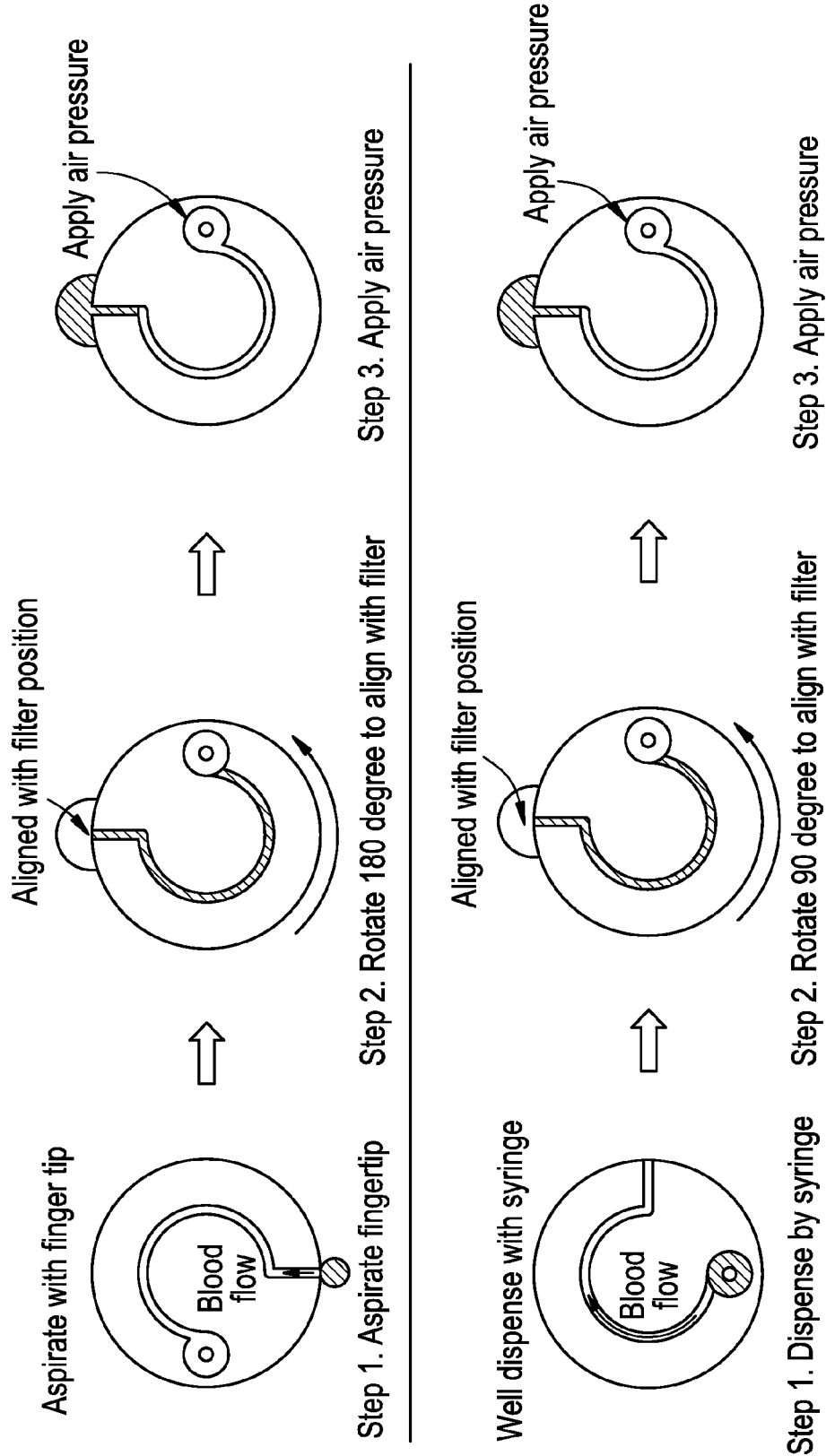

ROTATABLE DISK-SHAPED FLUID SAMPLE COLLECTION DEVICE

CROSS REFERENCE TO RELATED APPLICATIONS

This patent application claims priority to U.S. Provisional Application No. 61/790,961, filed Mar. 15, 2013, the disclosure of which is incorporated by reference in its entirety.

FIELD OF THE INVENTION

This present invention relates to a device for use in collecting and storing fluid samples, particularly biological samples, such as whole (unseparated) blood, serum, plasma and urine taken from the human or animal body. Such biological samples may be used in diagnostic and other biochemical tests. More particularly, the present invention relates to such a device which relies on capillary action for the collection of the fluid sample. The invention also relates to a working element comprising the fluid sample collection device. The present invention also relates to the field of diagnostic assays, and in particular to lateral flow assays where an analyte to be detected is present in a biological sample.

BACKGROUND

Fluid samples taken from the human or animal body are required for a wide variety of diagnostic and other biochemical tests, including the measurement of immunological reactions (immunoassays). There is accordingly a need for a device which can be conveniently used for collecting and storing such samples. Since the samples may pose a microbiological contamination or heath risk, the device used for their collection should not allow unintended release of the samples during storage, transportation or manipulation. The sample collection device is preferably disposable.

A known sample collection device for whole blood comprises an open-ended linear capillary tube formed of glass. The tube typically has an internal diameter of between one and two millimeters. To prevent clotting of the collected blood, the internal surface of the tube may be coated with a suitable anticoagulant such as heparin, which may also serve to reduce the contact angle between the sample and the side of the tube.

In use of the known device, the skin on the tip of a patient's finger is pierced by a lancet or other sharp piercing member. The blood so elicited is drawn into the linear tube by capillary action. The volume of the blood sample and the rate at which it is collected may be maximized by holding the tube with a generally horizontal orientation. The volume of the sample collected in this way is usually of the order 25-100 µL.

A problem associated with the blood sample collection device described above relates to the transportation and handling of the sample subsequent to its collection. In particular, when the orientation of the linear tube is changed, there is a risk that gravitational forces acting on the sample may exceed the intermolecular forces which maintain the sample in the tube, leading to the unintended release of a portion of the sample and the associated microbiological contamination or heath risk. This problem may be exacerbated when the linear tube is also subjected to accelerations caused by sudden movements or decelerations caused by small knocks, etc.

To prevent the unintended release of the sample, it is known to stopper one or both ends of the linear capillary tube, for example using silicone bungs or sealant. However, there remains a risk that a portion of the sample may be accidentally released before the ends of the tube have been sealed or after the seal has been removed for subsequent processing.

Another problem with capillary tubes is the absence of an easy method to identify the entification. This is especially important if the sample will be moved from the site of collection.

There are many challenges in designing a sample collection device to be use in conjuction with further sample manipulation such as diagnostic testing. These include: minimizing contamination due to premature dispense or leakage from the sample collection device; enabling collection directly from a patient (i.e., finger stick) as well as from peripheral sample collection devices such as collection tubes or syringes; insufficient transfer of the sample to the manipulation device; ensuring collection volume is sufficient for the sample manipulation process; sample evaporation; minimizing the ability to re-open the sample collection device to avoid contamination; or other sources of inaccuracies in the sample manipulation process.

Thus, there is a need in the art for an improved sample collection device for that overcomes the problems of the known art described above. In particular there is a need in the art for an improved sample collection device, which fluids are generally aqueous, and particularly such a device for which the risk of accidentally release of a portion of the sample subsequent to its collection may be reduced.

SUMMARY OF THE INVENTION

The present invention is directed to an assay device that alleviates one or more the foregoing problems described above.

One aspect of the invention is directed to a sample collection device for a fluid, the device comprising: a substantially disk-shaped body having a periphery; a capillary channel extending through the body and bounded by the periphery, having a first end and a second end, wherein the first end is adapted to draw the fluid into the channel by capillary action; a sample collection well located in the vicinity of the second end and in fluid communication with the capillary channel; and an axis of rotation extending through the center of the disk and which is substantially perpendicular to the major surface of the disk-shaped body. In a preferred embodiment, the sample collection device is adapted to rotate about the axis of rotation within a cartridge having a housing comprising an air vent in fluid communication with the capillary channel when the disk is rotated in a first position.

Another aspect of the invention is directed to a working element comprising: a sample collection device for a fluid, the device comprising: a substantially disk-shaped body having a periphery; a capillary channel extending through the body and bounded by the periphery, having a first end and a second end, wherein the first end is adapted to draw the fluid into the channel by capillary action; and an axis of rotation extending through the center of the disk and which is substantially perpendicular to the major surface of the disk-shaped body; and a cartridge having a housing comprising an air vent in fluid communication with the capillary channel when the disk is rotated in a first position, and containing a sample manipulation device, wherein the sample collection device is rotatably positioned within the cartridge housing and at least a portion of the side and top surface of the disk are exposed for application of sample. In a preferred embodiment, the sample manipulation device is an analytical chamber having an analytical reagent thereon, such as a lateral flow assay device.

Another aspect of the invention is directed to a method for collecting a sample comprising: providing a working element comprising: a sample collection device for a fluid, the device comprising: a substantially disk-shaped body having a periphery; a capillary channel extending through the body and bounded by the periphery, having a first end and a second end, wherein the first end is adapted to draw the fluid into the channel by capillary action; a sample collection well located in the vicinity of the second end and in fluid communication with the capillary channel; and an axis of rotation extending through the center of the disk and which is substantially perpendicular to the major surface of the disk-shaped body; and a cartridge having a housing comprising an air vent in fluid communication with the capillary channel when the disk is rotated in a first position, and containing a sample manipulation device, wherein the sample collection device is rotatably positioned within the cartridge and at least a portion of the side and top surface of the disk are exposed for application of sample; rotating the sample collection device to a second position to position the first end into contact with a sample, or rotating the sample collection device into a third position to position the sample collection well into contact with a sample; collecting the sample into the sample collection device; rotating the sample collection device to the first position to position the first end into position with sample manipulation device; and applying air pressure to the air vent to force the sample across the barrier and into contact with the sample manipulation device.

Another aspect of the invention is directed to a method of performing an assay on a liquid sample for the presence or concentration of one or more analyte(s) or control(s), on the assay device described above, comprising: rotating the sample collection device to a second position to position the first end into contact with the sample, or rotating the sample collection device into a third position to position the sample collection well into contact with the sample; collecting the sample into the sample collection device; rotating the sample collection device to the first position to position the first end into position with the assay device; and applying air pressure to the air vent to force the sample into contact with a sample addition zone of the assay device; moving the sample by capillary action through a fluid flow path into a reagent zone where it dissolves one or more reagents; flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analytes or controls.

Further objects, features and advantages of the present invention will be apparent to those skilled in the art from detailed consideration of the preferred embodiments that follow.

BRIEF DESCRIPTION OF THE DRAWINGS

FIG. 5 shows the positioning of the sample collection device in various sample collection/aspiration and dispense positions.

DETAILED DESCRIPTION OF PREFERRED EMBODIMENTS

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" herein means a volume of a liquid, solution or suspension, intended to be acted upon by a sample manipulation device. Preferably, the sample is subjected to qualitative or quantitative determination of any of its properties, such as the presence or absence of a component, the concentration of a component, etc. Typical samples in the context of the present invention are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This is only a small example of samples that can be used in the present invention.

Non-biological samples can be aqueous or non-aqueous, for example waste water samples for environmental testing and solutions having organic solvents, such as alcohols for chemical processing.

One aspect of the invention is directed to a sample collection device for collecting a sample, such as a blood or blood-based sample, and delivering it to a sample manipulation device that overcomes at least some of the disadvantages of known sample collection devices.

Figure 1A:
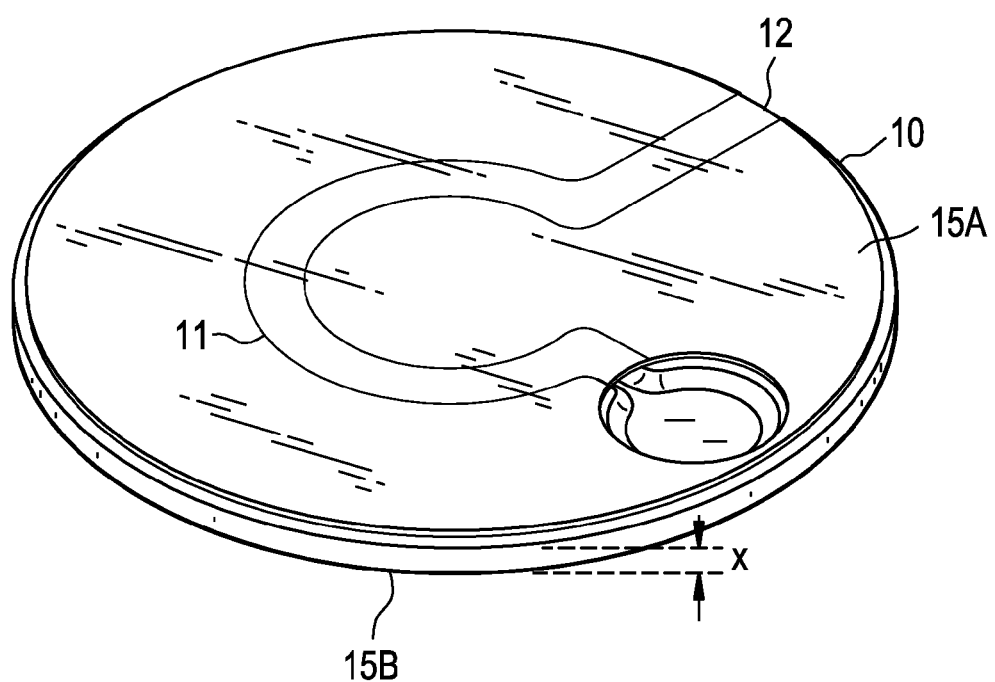
FIGS. 1A-C show various views of a sample collection device according to one embodiment of the invention.
Figure 1B:
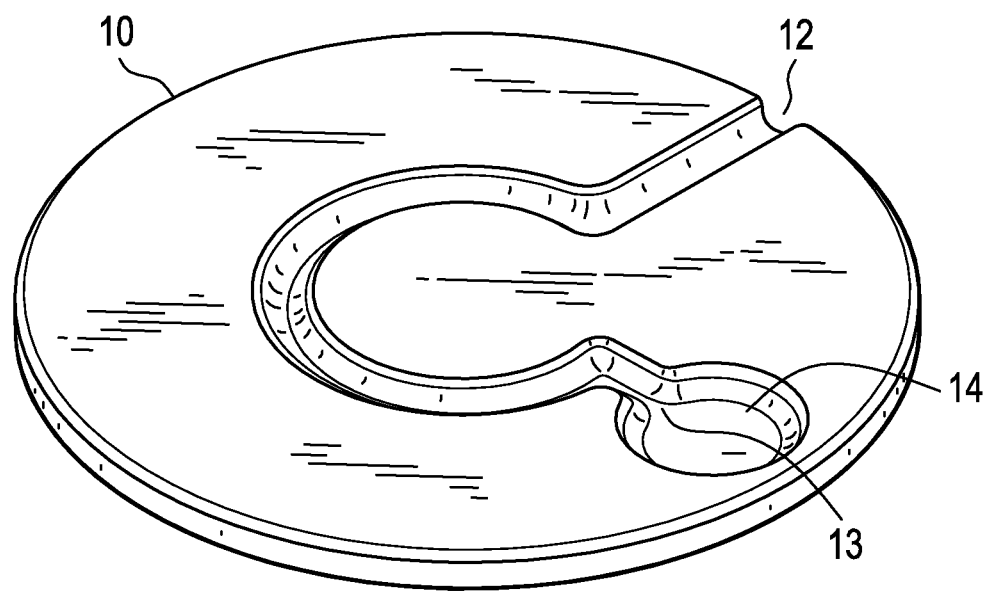
Figure 1C:
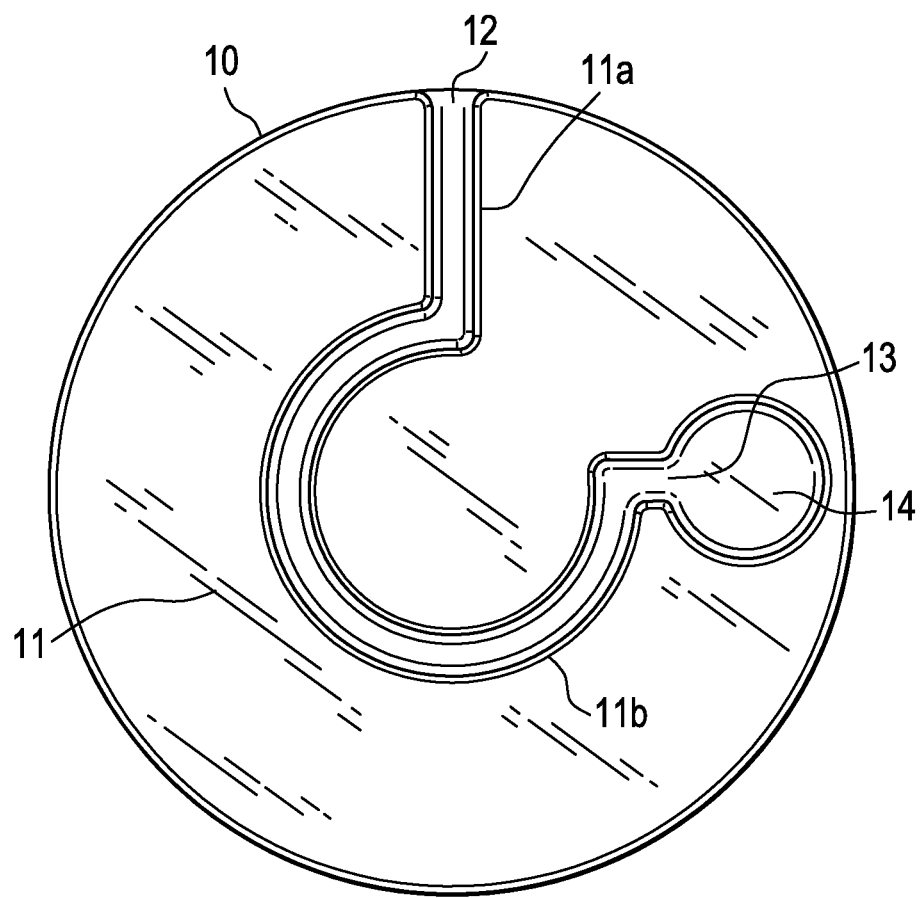

FIGS. 1A-1C show a preferred embodiment of the sample collection device 10. The device is preferably substantially disk-shaped as shown in FIG. 1A. The diameter and thickness x of the device can be any suitable dimension capable of holding a sufficient amount of sample. The term "substantially disk-shaped" as used herein means any planar shape that is capable of rotating within the housing of a working element as described below and does not necessarily have to be circular. The sample collection device can be made from any suitable material, such as a plastics material, such as polymethyl methacrylate (other plastic materials can include polystyrene, polyethylene, cyclic olefins, acrylics, or moldable polyesters), and is preferably formed by molding such as injection molding. Other possible materials include glass, metal, ceramic, etc. In a preferred embodiment, the device is at least partially transparent for the flow of the fluid in the capillary channel can be observed.

Positioned within and bounded by the periphery of the disk-shaped body is a capillary channel 11 having dimensions sufficient to hold a desired amount of sample. The capillary channel may have any cross-sectional shape, for example circular or substantially semi-circular ("U" shaped) cross-sections. A substantially semi-circular cross-sectional shape is particularly convenient if the passage is to be defined between two flat components in contact with each other, since only one of the components then needs to be grooved. FIGS. 1A and 1B show a particularly preferred embodiment, where the disk is made of two flat pieces that are joined together to form the capillary channel. FIG. 1A shows the device with both of the pieces joined. In this embodiment, the top piece 15A is joined to the bottom piece 15B, such as by an adhesive. The top piece is preferably a hydrophilic tape. FIG. 15B shows only the bottom piece 15B with the U-shaped channel. The dimensions of the channel are selected such that capillary flow of the fluid being sampled will be achieved. For a biological sample, such as blood or plasma, the channel will preferably have a cross-section that is in the range of 0.25-3.0 mm$^2$, preferably 0.5-3.0 mm$^2$. The volume of the capillary channel may be in the range 10 µL to 100 µL, preferably in the range 10 µL to 70 µL, and more preferably 20 µL to 50 µL. The length of the capillary channel is preferably 20 mm-100 mm. For aqueous samples, the capillary channel is preferably treated to render the surface hydrophilic, if it is not already. In addition, for biological samples, such as whole blood, other additives can be included to preserve the biological sample, such as anti-coagulants such as heparin, sodium citrate, or EDTA.

The capillary channel has a first end and a second end. The first end 12 of the channel is adapted to draw fluid into the capillary channel. Preferably, the first end opens on the side surface of the disk-shaped body in order to simplify sample collection from a live subject as describe in more detail below. However, in some embodiments, it may be preferable to have the first end opening onto the top or bottom surface of the disk-shaped collection device.

Located in fluid communication with the second end 13 is a sample collection well 14. The sample collection well 14 preferably opens onto the top surface of the disk and can simply be a concavity in the top of the disk. The collection well is preferably hydrophilic to assist in acquiring and retaining the sample. Various hydrophilic coatings and materials can be used to render the well hydrophilic, including the same materials described with respect to the capillary channel. In a preferred embodiment, the sample collection well will align with a port or vent in the cartridge, which is connected to a source of air pressure to pressurize the capillary channel as described in more detail below. In a preferred embodiment, the well is be sized to hold approximately the same volume as the channel, so as to prevent possible sample overload.

The shape of the capillary channel can be straight or more preferably at least partially non-linear. By having at least a non-linear portion the maximum gravitational forces which can act on the collected sample (with the device in any orientation) are reduced, as compared to a sample in a conventional linear capillary tube of comparable type. In a preferred embodiment, the capillary channel has a semi-circular shape, such as the shape of a shepherd's staff as shown in FIG. 1C, with a straight portion 11a extending radially inward from the first end 12 and forming a semi-circular portion 11b that ends at the second end 13.

The sample collection device is preferably part of a working element 20 for performing some aspect of sample manipulation, such as a diagnostic assay, described in more detail below. Other sample manipulation could include microfluidics devices that can be used to obtain a variety of interesting measurements including molecular diffusion coefficients, fluid viscosity, pH, chemical binding coefficients and enzyme reaction kinetics. Other applications for microfluidic devices include capillary electrophoresis, isoelectric focusing, flow cytometry, sample injection of proteins for analysis via mass spectrometry, PCR amplification, DNA analysis, cell manipulation, cell separation, cell patterning and chemical gradient formation.

Figure 2A:
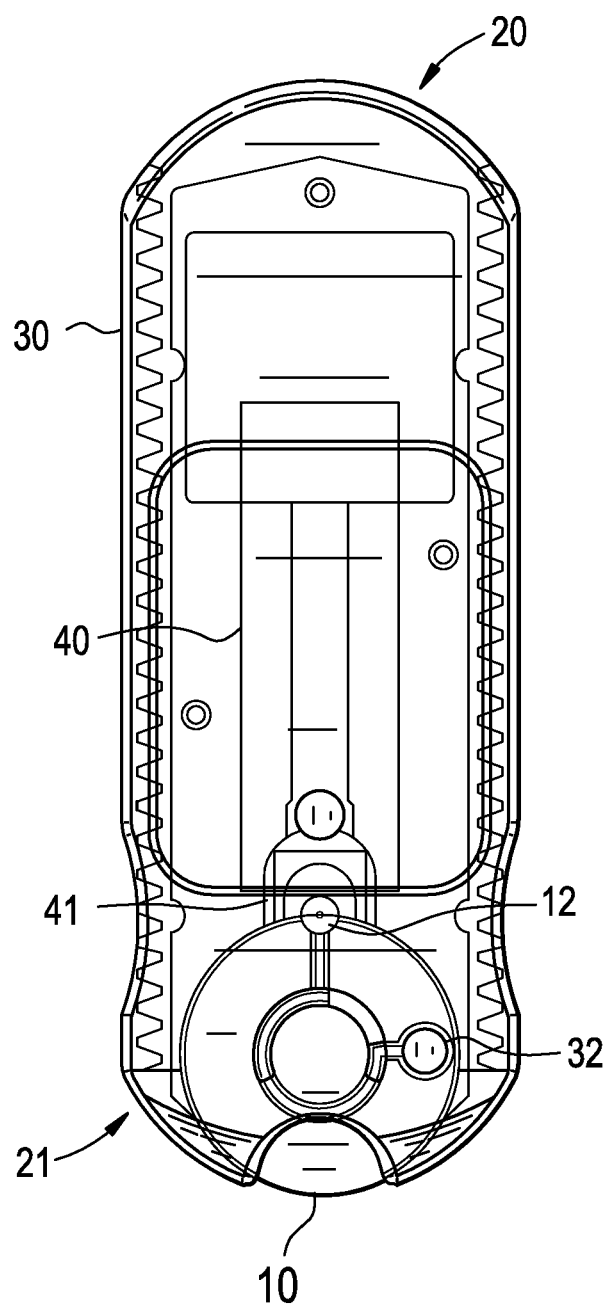
FIG. 2A shows a cutaway view of a working element according to one embodiment of the invention.
Figure 2B:
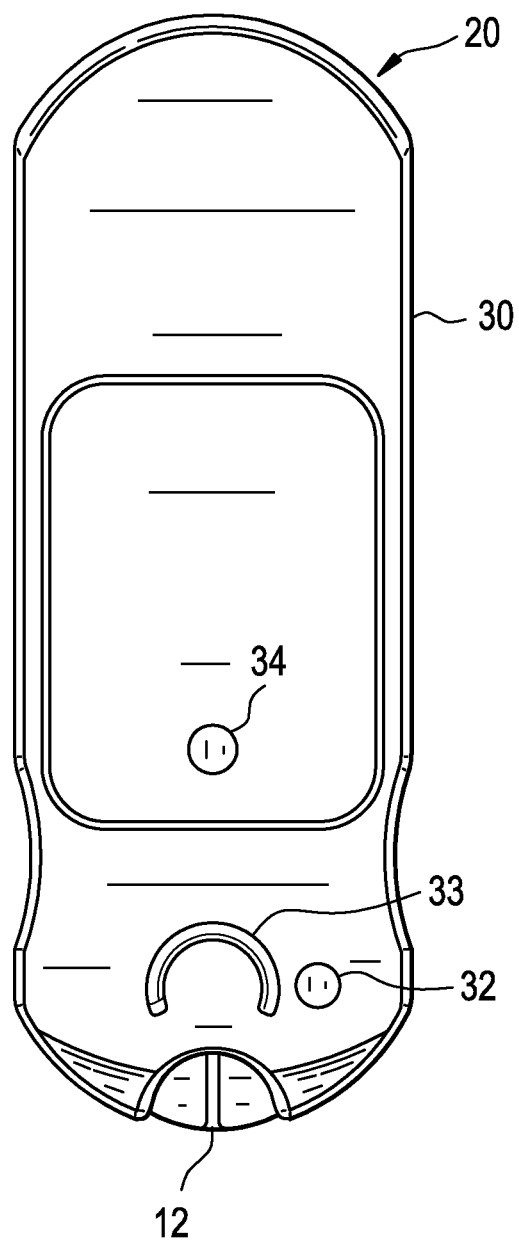
FIG. 2B shows a top planar view of a working element according to one embodiment of the invention.
Figure 3:
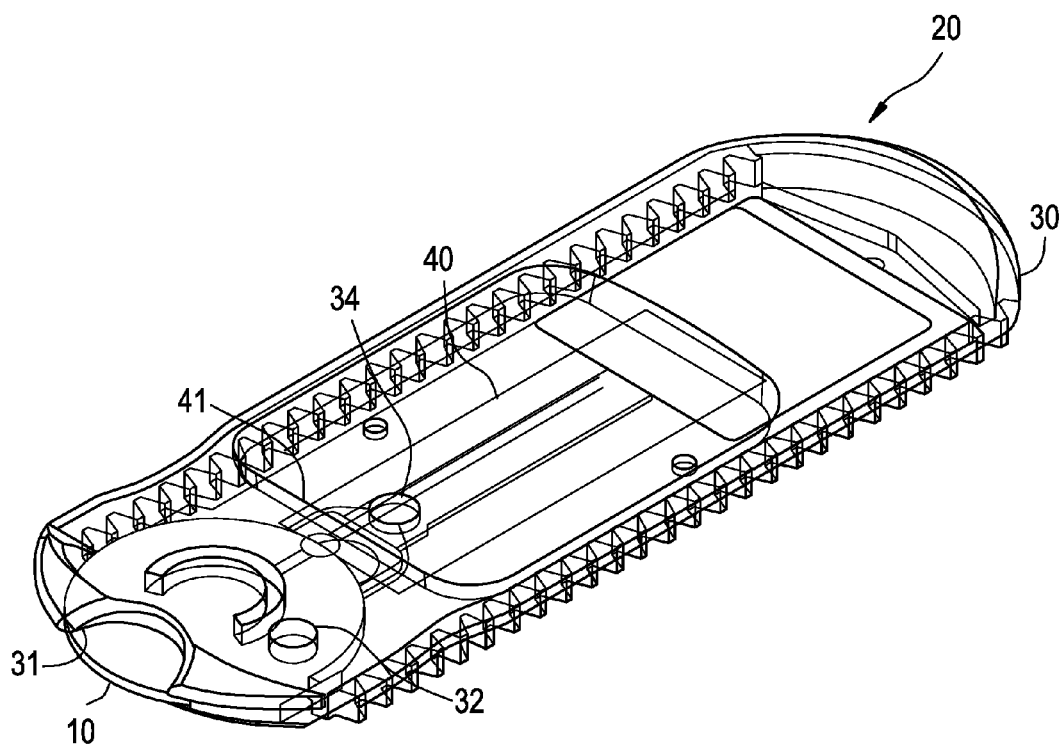
FIG. 3 shows a cutaway perspective view of a working element according to one embodiment of the invention.

The working element 20 includes a cartridge 30 for housing various components of the working element. FIG. 2A is a top cut away view of the working element 20 and its components. The sample collection device 10 is located at a first end 21 of the working element as shown in the lower portion of FIG. 2A and in more detail in FIG. 3. The sample collection device is preferably fully contained within the cartridge 30, except for a small recess 31 in the cartridge housing which forms a corresponding notch in the cartridge to expose a portion of the sample collection device 10. In FIG. 2B, the sample collection device is positioned within the cartridge such that the first end 12 is exposed in the recess 31. In FIGS. 2A and 3, neither the first or second end of the sample collection device is exposed in recess 31. Alternatively, the sample collection device 10 can be held within the cartridge housing such that a portion of the device 10 protrudes from the end 21 of the working element without any recess.

The cartridge housing is preferably formed of two molded halves that can be snap fit together or welded together. Alternatively, the cartridge housing can include molded top cover and a laminated film.

Other features of the cartridge housing include an air vent or port 32 for application of air pressure to the capillary channel. As described above, the vent 32 aligns with the sample collection well 14 when the sample collection device is rotated to a dispense position (described below), to provide fluid communication between the capillary channel and a source of compressed air (not shown).

The cartridge housing can also include an opening 33 that roughly corresponds to the shape of the capillary channel to allow visual or other observation of the sample in the channel. In addition, an opening 34 can be provided that provides access to the sample manipulation device 40 of the working element. For example, if the sample manipulation device is a lateral flow diagnostic assay the opening 34 can be used to apply a wash fluid to the assay.

The sample collection device 10 is rotatably held within the cartridge housing 30, whereby it can rotate between various aspirate and dispense positions. In a preferred embodiment, the sample collection device can have pins extending above and below from the center. The pins are rotatably held by corresponding features in both halves of the cartridge, such as slots (not shown). Alternatively, the collection device can have slot or hole in the center through which a pin or rod from the cartridge extends therethrough.

The working element also includes a sample manipulation device 40 for conducting further analysis or processing of a sample. Such processing or analysis can include the microfluidics applications described above. As noted above, a particularly preferred sample manipulation is a lateral flow diagnostic assay described in more detail below with reference to FIGS. 6-8. The sample manipulation device 40 may include a pre-manipulation portion 41, such as a filter for filtering whole blood. After application of the sample to the sample manipulation device 40, the working element can be further used in devices, such as an analyzer for detecting and analyzing a single, or a chemical processor for further processing of the sample, or any other type of microfluidics devices described above. A particularly preferred analyzer is a fluorometer.

The sample manipulation device 40 and optionally the pre-manipulation portion 41 are in fluid communication with the first end 12 when the sample collection device 10 is in a first or dispense position as described below.

Figure 4A:
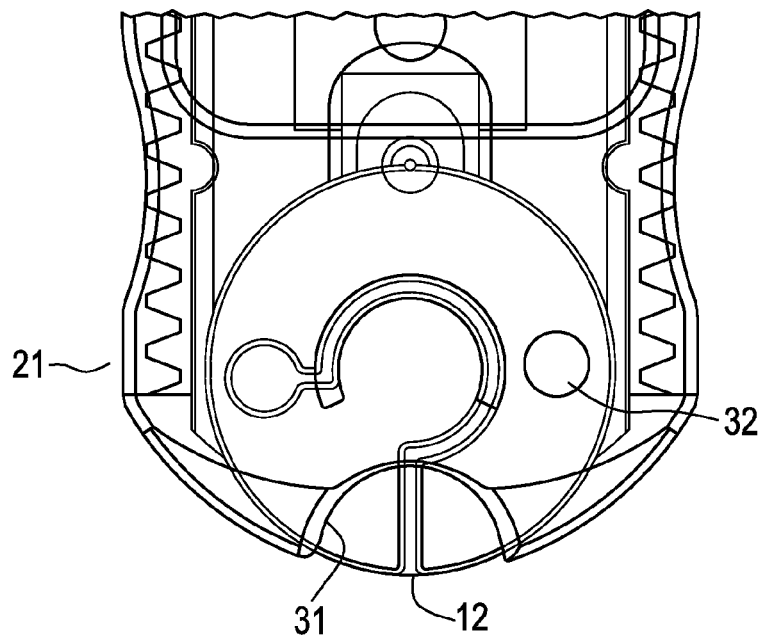
FIGS. 4A-C show the sample collection device in the working element in various collection and dispense positions.
Figure 4B:
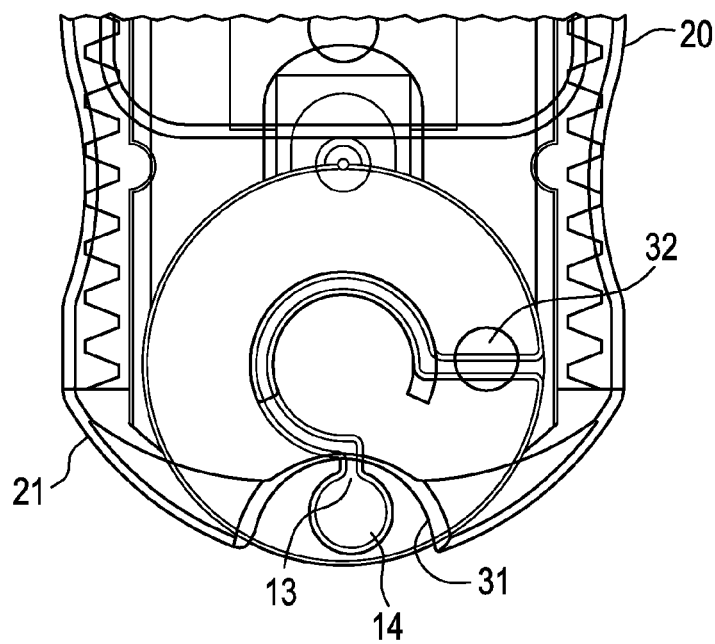

As noted above, the sample collection device is rotatable within the cartridge housing. This allows the device to move from multiple sample collection or aspiration positions to position(s) where the sample can be dispensed to the sample manipulation device or pre-manipulation portion. FIGS. 4A and 4B show the sample collection device in two possible sample collection or aspiration positions. The FIG. 4A position or the second position shows the first end 12 of the capillary channel 11 exposed to the outside environment through the recess 31, while the second end 13 is within the cartridge housing. In the second position the first end 12 can be directly contacted with the sample to be collected, such as a drop of blood from a finger stick. By capillary forces, the sample will be drawn or aspirated into the capillary channel. The progression of the sample into the channel can be observed by the opening 33.

Figure 4C:
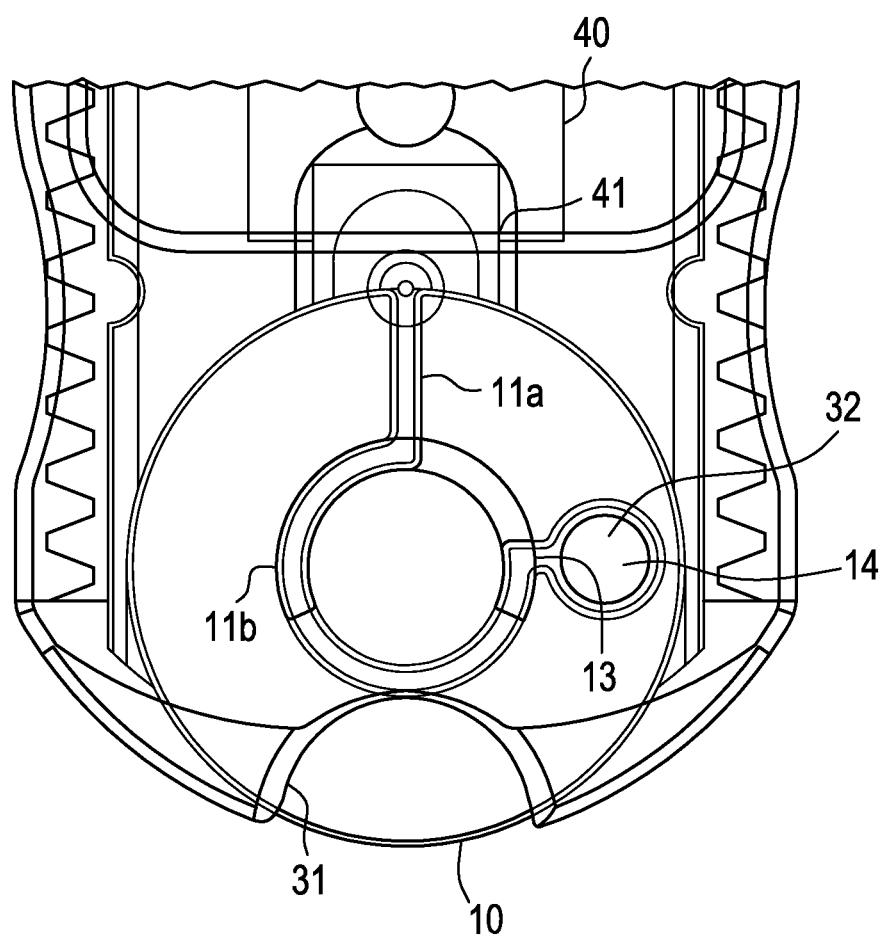

When a desired amount of sample has been collected, the sample collection device can then be rotated to the first or dispense position as shown in FIG. 4C. In a preferred embodiment, the rotation is approximately 180 degrees. In the first position, the first end 12 of the capillary channel is rotated to position it with the sample manipulation device 40 or pre-manipulation portion 41. Due to the preferred shepherd's staff design when the first end 12 is positioned at the sample manipulation device 40 or pre-manipulation portion 41, the second end 13 is in fluid communication with air vent or port 32. Of course, if another shape for the capillary channel is selected the air vent or port would be positioned such that it would line-up or be in fluid communication with the second end 13. A source of compressed air (not shown) is then applied and the sample is forced to move from the capillary channel through the first end 12 and into the sample manipulation device 40 or pre-manipulation 41 portion of the working element. The compressed air may be supplied by any suitable means, such as by a rubber diaphragm that may or may not be part of an instrument or processing apparatus that further handles the working element.

Instead of rotating the first end 12 directly to the first or sample dispense position, it is possible to instead rotate the first end 12 to an intermediate position, such that it is neither exposed to the environment through the recess 31 or in fluid communication with the sample manipulation device 40 or pre-manipulation portion 41. The first and second ends of the capillary channel are contained within the cartridge housing and preferably would be in contact with a sealing material positioned within cartridge housing, such as a piece of elastomer, that effectively temporarily seals or plugs the capillary channel until the sample is ready for use. This would prevent premature transfer of sample to the sample manipulation device, such as by gravity during handling.

The FIG. 4B position or the third position shows the second end 13 of the capillary channel 11 exposed to the outside environment through the recess 31, while the first end 12 is within the cartridge housing. In the third position the second end 13 having the sample collection well 14 can have sample applied to it such as by a syringe filling the sample collection well 14. By capillary forces, the sample will be drawn from the sample well into the capillary channel. The progression of the sample into the channel can be observed by the opening 33.

When a desired amount of sample has been collected, the sample collection device can then be rotated to the first or dispense position as shown in FIG. 4C and the sample dispensed in the manner described above. In a preferred embodiment, the rotation is approximately 90 degrees.

As also described above, instead of rotating the first end 12 directly to the first or sample dispense position, it is possible to instead rotate the first end 12 to an intermediate position, such that it is neither exposed to the environment through the recess 31 or in fluid communication with the sample manipulation device 40 or pre-manipulation portion 41. The first and second ends of the capillary channel are contained within the cartridge housing and preferably would be in contact with a sealing material positioned within cartridge housing, such as a piece of elastomer, that effectively temporarily seals or plugs the capillary channel until the sample is ready for use. This would prevent premature transfer of sample to the sample manipulation device, such as by gravity during handling.

The top row of FIG. 5 shows another view of sample collection or aspiration with the first end of the capillary channel followed by rotation from the second position to the first or dispense position, where air pressure is applied at the second end of the capillary channel to move the sample from the capillary channel to the sample manipulation or pre-manipulation portion, in this case, a whole blood filter.

Likewise, the bottom row of FIG. 5 shows another view of sample collection with the second end of the capillary channel followed by rotation from the third position to the first or dispense position, where air pressure is applied at the second end of the capillary channel to move the sample from the capillary channel to the sample manipulation or pre-manipulation portion, in this case, a whole blood filter.

In a preferred embodiment, the sample manipulation part of the cartridge or a cassette is a diagnostic assay. Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture.

Examples of diagnostic assays include, but are not limited to, the determination of analytes, also called markers, specific for different disorders, e.g. chronic metabolic disorders, such as blood glucose, blood ketones, urine glucose (diabetes), blood cholesterol (atherosclerosis, obesity, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

A common type of disposable assay device includes a zone or area for receiving the liquid sample, a conjugate zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

Another type of assay device is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

Figure 6:
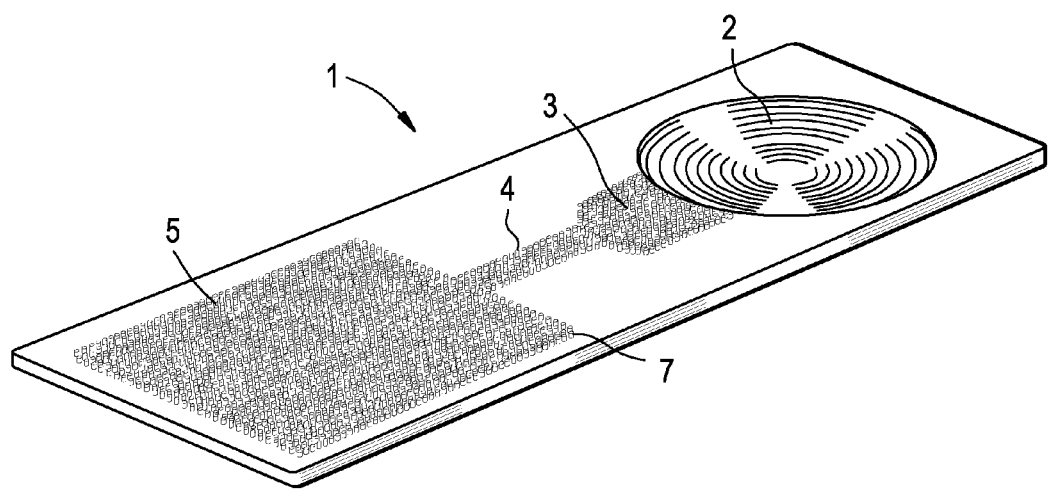
FIG. 6 shows an embodiment of an assay device usable in the present invention.

A non-porous assay device is shown in FIG. 6. The assay device 1, has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay. Unbound dissolved conjugate material will be swept past the detection zone into the at least one wicking zone 5.

An instrument such as that disclosed in US 20060289787A1, US20070231883A1, U.S. Pat. No. 7,416,700 and U.S. Pat. No. 6,139,800 all incorporated by reference in their entireties is able to detect the bound conjugated analyte and label in the reaction zone. Common labels include fluorescent dyes that can be detected by instruments which excite the fluorescent dyes and incorporate a detector capable of detecting the fluorescent dyes. Such instruments have a read window that has a width that is typically on the order of 1 mm, which is a generally sufficient width to read enough signal, subject to an adequate width of the conjugate plume.

Figure 7:
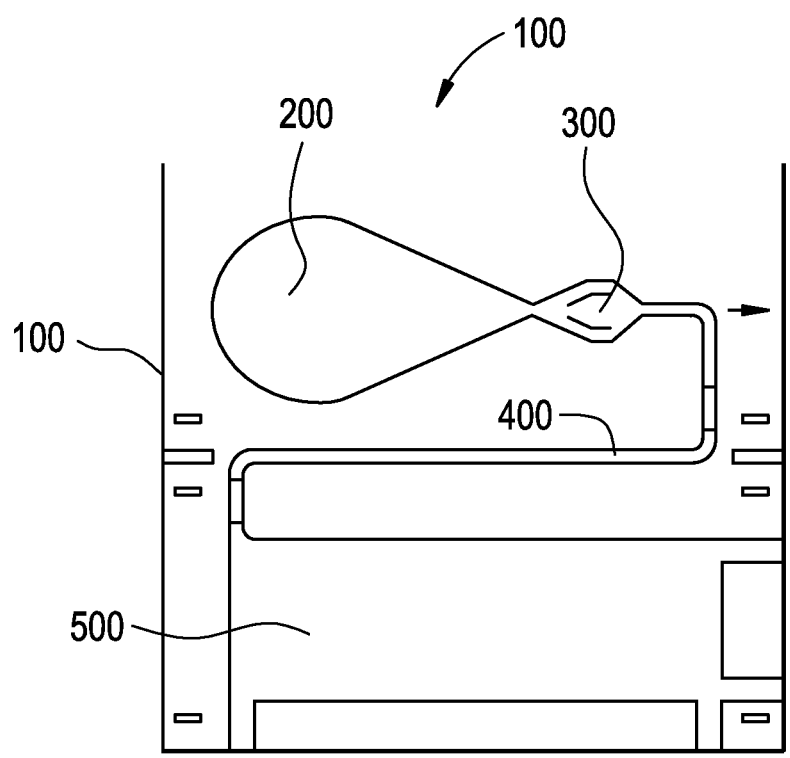
FIG. 7 shows another embodiment of an assay device usable in the present invention.
Figure 8:
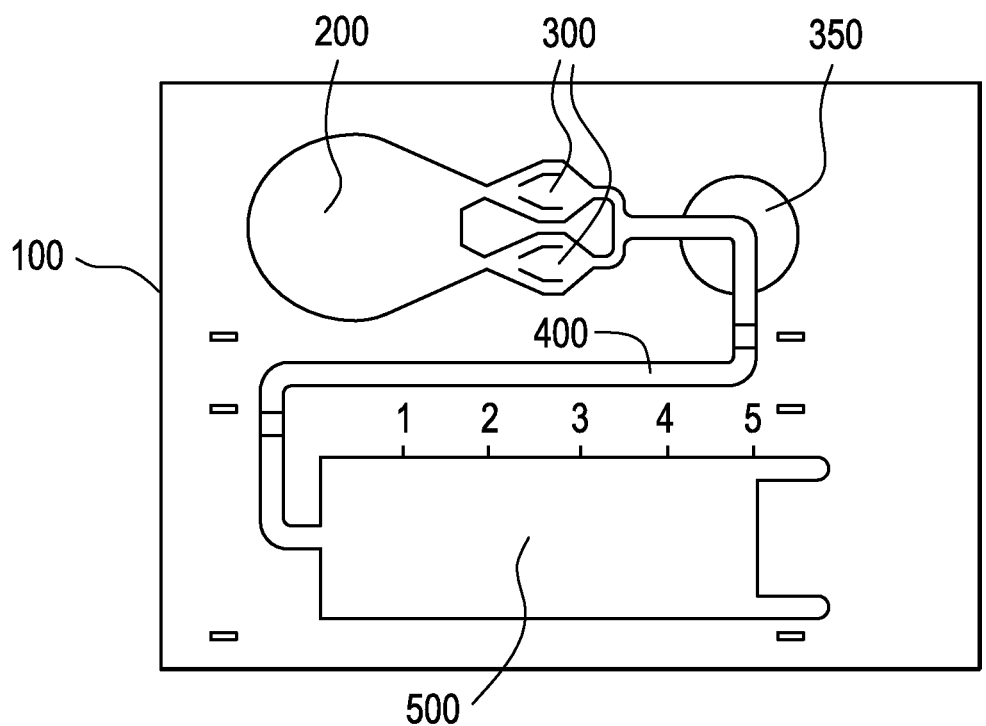
FIG. 8 shows another embodiment of an assay device usable in the present invention.

FIG. 7 shows a schematic view of a preferred lateral flow assay device usable as the sample manipulation device 40. The assay device 100 has at least one sample zone (also referred to as sample addition zone) 200, at least one reagent zone 300, at least one detection zone 400, and at least one wicking zone 500. The zones form a flow path by which sample flows from the sample addition zone to the wicking zone.

Components of the assay device and any other part of the working element (i.e., a physical structure of the device whether or not a discrete piece from other parts of the device) can be prepared from copolymers, blends, laminates, metalized foils, metalized films or metals. Alternatively, device components can be prepared from copolymers, blends, laminates, metalized foils, metalized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the assay device is injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

The flow path can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. FIG. 6 shows projections 7.

In one embodiment the flow path is at least partially open. In another embodiment the flow path is entirely open. Open means that there is no lid or cover at a capillary distance. Thus the cover, if present as a physical protection for the flow path, does not contribute to the capillary flow in the flow path. An open lateral flow path is described for example in the following published applications: WO 2003/103835, WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in US 2006/0285996, which is incorporated by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 µm, preferably about 30 to about 100 µm, a diameter of about 10 to about 160 µm, preferably 40 to about 100 µm, and a gap or gaps between the projections of about 3 to about 200 µm, preferably 5 to about 50 µm or 10 to 50 µm from each other. The flow channel may have a length of about 5 to about 500 mm, preferably about 10 to about 100 mm, and a width of about 0.3 to about 10 mm, preferably about 0.3 to about 3 mm, preferably about 0.5 to 1.5, and preferably about 0.5 to 1.2 mm.

While most detection will occur in the detection zone portion of the fluid flow path, it is also possible that detection may occur in other parts of the device. For example, non-invasive, non-reactive sample integrity measurements may occur between the sample zone and the reagent zone or reagent addition zone, preferably after a filter element, if present. Other measurements may include blanks reads, one part of a two part reaction sequence as for measuring both hemoglobin and glycated hemoglobin for determination of HbA1c, etc.

The liquid sample zone 200, also referred to as the liquid sample addition zone, receives sample from the sample collection device 10. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, or preferably through projections, such as micro-pillars, as shown in FIG. 6. In those devices that can use finger stick volumes of blood, the sample can be directly touched off from the finger, or by a capillary pipette.

Located between the sample addition zone and the detection zone is a reagent zone 300. The reagent zone can include reagent material(s) integrated into the analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. In one preferred embodiment, the reagent zone includes conjugate material. The term conjugate means any moiety bearing both a detection element and a binding partner.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}I$ and $^{32}P$.

Suitable enzymatic labels are, for instance, but are not limited to, horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in an "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone and before the detection zone is a reagent addition zone. The reagent addition zone is shown as 350 in FIG. 8. The reagent addition zone can allow addition of a reagent externally from the device. For example, the reagent addition zone may be used to add an interrupting reagent that may be used to wash the sample and other unbound components present in the fluid flow path into the wicking zone.

In a preferred embodiment the reagent addition zone 350 is located after the reagent zone 300.

Downstream from the liquid sample zone and the reagent zone is the detection zone 400 which is in fluid communication with the sample addition zone. The detection zone 400 may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above and in co pending application entitled "Lower Volume Assay Device Having Increased Sensitivity," Ser. No. 13/744,617, filed on Jan. 20, 2013 and incorporated by reference in its entirety, are significantly narrower, e.g., 1.5 mm or less, preferably 0.5 to 1.2 mm.

The detection zone is where any detectable signal is read. In a preferred embodiment attached to the projections in the detection zone are capture elements. The capture elements can include binding partners for the conjugate or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used for assays that include one or more markers. In the event of multiple detection zones, the capture elements can include multiple capture elements, such as first and second capture elements. The conjugate can be pre-deposited on the assay device, such as by coating in the reagent zone. Similarly the capture elements can be pre-deposited on the assay device on the detection zone. Preferably, both the detection and capture elements are pre-deposited on the assay device, on the detection zone and detection zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the detection zone or those added through the reagent addition zone. The reagent in the sample flowing from the reagent zone, but before the reagent addition zone is considered to be a reagent plume. The reagent plume can include the conjugate having both the detection element and binding partner, in which case it is often referred to as a conjugate plume.

Downstream from the detection zone is a wicking zone in fluid communication with the detection zone. The wicking zone is an area of the assay device with the capacity of receiving liquid sample and any other material in the flow path, e.g., unbound reagents, wash fluids, etc. The wicking zone provides a capillary force to continue moving the liquid sample through and out of the detection zone. The wicking zone can include a porous material such as nitrocellulose or can be a non-porous structure such as the projections described herein. The wicking zone can also include non-capillary fluid driving means, such as using evaporative heating or a pump. Further details of wicking zones as used in assay devices according to the present invention can be found in patent publications US 2005/0042766 and US 2006/0239859, both of which are incorporated herein by reference in their entireties. Wicking zones are also described in copending patent application entitled "Controlling Fluid Flow Through An Assay Device," Ser. No. 13/744,641, filed on Jan. 18, 2013, and incorporated by reference in its entirety.

Preferably the entirety of the flow path including the sample addition zone, the detection zone and the wicking zone includes projections substantially vertical in relation to the substrate, and having a height, diameter and reciprocal spacing capable of creating lateral flow of the sample in the flow path.

In any of the above embodiments, the device is preferably a disposable assay device. The assay device may be contained in a housing for ease of handling and protection. If the assay device is contained in such a housing, the housing will preferably include a port for adding sample to the assay device.

The assay device of the present invention can be used with a device for reading (a reader) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US 2007/0231883 and U.S. Pat. No. 7,416,700, both of which are incorporated by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

The assay device along with the rest of the cartridge can be used to perform an assay on a liquid sample for the detection of one or more analytes of interest. A liquid sample containing the analyte(s) of interest is collected using the sample collection device as described above and is then dispensed onto the sample zone of the assay device. The sample moves by capillary action through an optional filter and into the reagent zone where it encounters the multiple reagent materials. The sample flows past the first, second and third reagent material. The reagent material flowing past the second and third reagent materials form second and third reagent plumes along the edges of the reagent cell. The sample flowing past the first reagent material forms a first reagent plume long the line of symmetry of the reagent cell. The first, second and third reagent material combine upon leaving the reagent cell to form a combined reagent plume.

Next the sample and reagent plume move by capillary action into the detection zone. There a signal representative of the presence or concentration of the analyte(s) or control is produced. In a preferred embodiment the sample or the one or more reagents having a detection element is captured having in the detection zone, such as by antibodies on the surface of the detection zone and a signal representative of the presence or concentration of the analyte(s) or control(s) is produced.

The reader as described above is then used to read the signal that is produced by the detection element to determine the presence or concentration of the analyte(s). The sample moves from the detection zone and into the wicking zone. The reader may read the signal immediately or a short time after the sample has moved through the detection zone. Also, one or more washes may follow the sample through the device to wash any unbound detection element away from the detection zone. The cartridge 20 containing the lateral flow assay device can be inserted into the reader either before or after the sample has been dispensed to the sample collection zone. In those embodiments where a source of compressed air is used to dispense the sample, the cartridge can first be inserted into the reader and the compressed air can then be used to force sample from the sample collection device to the assay device.

The method, assay device, and reader according to an embodiment of the invention have many advantages, mainly related to the improved detection kinetics of the immunochemical reactions and the increased sensitivity of the assay. It is to be understood that this invention is not limited to the particular embodiments shown here.

ADDITIONAL EMBODIMENTS

1. A sample collection device for a fluid sample, the device comprising: a substantially disk-shaped body having a periphery; a capillary channel extending through the body and bounded by the periphery, having a first end and a second end, wherein the first end is adapted to draw the fluid into the channel by capillary action; a sample collection well located in the vicinity of the second end and in fluid communication with the capillary channel; and an axis of rotation extending through the center of the disk and which is substantially perpendicular to the major surface of the disk-shaped body.

2. A sample collection device as disclosed in embodiment 1, wherein the sample collection device is adapted to rotate about the axis of rotation within a cartridge having a housing comprising an air vent in fluid communication with the capillary channel when the disk is rotated in a first position.

3. A sample collection device as disclosed in embodiment 2, wherein the air vent is located in the vicinity of and in fluid communication with the second end of the capillary channel when the disk is rotated in a first position.

4. A sample collection device as disclosed in embodiment 1, wherein the opening of the first end is located on the side surface of the disk and the well is located on the top surface of the disk.

5. A sample collection device as disclosed in embodiment 1, wherein the capillary channel is non-linear.

6. A sample collection device as disclosed in embodiment 5, wherein the capillary channel has a semi-circular shape.

7. A sample collection device as disclosed in embodiment 6, wherein the capillary channel has a staff shape.

8. A sample collection device as disclosed in embodiment 1, wherein the first end is hydrophilic.

9. A sample collection device as disclosed in embodiment 8, wherein the first end is provided with a hydrophilic coating.

10. A working element comprising: a sample collection device for a fluid sample, the device comprising: a substantially disk-shaped body having a periphery; a capillary channel extending through the body and bounded by the periphery, having a first end and a second end, wherein the first end is adapted to draw the fluid into the channel by capillary action; and an axis of rotation extending through the center of the disk and which is substantially perpendicular to the major surface of the disk-shaped body; and a cartridge having a housing comprising an air vent in fluid communication with the capillary channel when the disk is rotated in a first position, and containing a sample manipulation device, wherein the sample collection device is rotatably positioned within the cartridge housing and at least a portion of the side and top surface of the disk are exposed for application of sample.

11. A working element as disclosed in embodiment 10, wherein the air vent is located in the vicinity of and in fluid communication with the second end of the capillary channel when the disk is rotated in a first position.

12. A working element as disclosed in embodiment 10, wherein the sample manipulation device includes a pre-manipulation portion.

13. A working element as disclosed in embodiment 10, wherein the sample manipulation device is an analytical chamber having an analytical reagent thereon.

14. A working element as disclosed in embodiment 13, wherein the analytical chamber is a lateral flow assay device.

15. A working element as disclosed in embodiment 10, wherein the sample collection device is located at a first end of the cartridge housing and the portion of the side and top surface exposed are exposed at the first end of the cartridge.

16. A working element as disclosed in embodiment 15, wherein sample collection device protrudes from the first end of the cartridge housing.

17. A working element as disclosed in embodiment 15, wherein the sample collection device is fully contained within the cartridge housing and a portion of the cartridge housing is recessed from the first end to form a notch exposing the side and top surface of the disk.

18. A working element as disclosed in embodiment 15, wherein when the sample collection device is rotated at a second position, the first end of the capillary channel is exposed at the first end of the cartridge.

19. A working element as disclosed in embodiment 15, wherein when the sample collection device is rotated at a third position, the second end of the capillary channel is exposed at the first end of the cartridge.

20. A working element as disclosed in embodiment 10, wherein when the disk is rotated in the first position, the first end is in communication with the sample manipulation device.

21. A working element as disclosed in embodiment 20, wherein the air vent is adapted to be connected to a source of air pressure to force sample from the capillary channel through the first end and into the sample manipulation device.

22. A method for collecting a sample comprising: providing a working element comprising: a sample collection device for a fluid sample, the device comprising: a substantially disk-shaped body having a periphery; a capillary channel extending through the body and bounded by the periphery, having a first end and a second end, wherein the first end is adapted to draw the fluid into the channel by capillary action; a sample collection well located in the vicinity of the second end and in fluid communication with the capillary channel; and an axis of rotation extending through the center of the disk and which is substantially perpendicular to the major surface of the disk-shaped body; and a cartridge having a housing comprising an air vent in fluid communication with the capillary channel when the disk is rotated in a first position, and containing a sample manipulation device, wherein the sample collection device is rotatably positioned within the cartridge and at least a portion of the side and top surface of the disk are exposed for application of sample; rotating the sample collection device to a second position to position the first end into contact with a sample, or rotating the sample collection device into a third position to position the sample collection well into contact with a sample; collecting the sample into the sample collection device; rotating the sample collection device to the first position to position the first end into position with the sample manipulation device; and applying air pressure to the air vent to force the sample across the barrier and into contact with the sample manipulation device.

23. A method as disclosed in embodiment 22, wherein the air vent is located in the vicinity of and in fluid communication with the second end of the capillary channel when the disk is rotated in a first position.

24. A method as disclosed in embodiment 22, wherein the sample manipulation device includes a pre-manipulation portion.

25. A method as disclosed in embodiment 22, wherein the step of rotating the sample collection device to position the first or second end into contact with a sample further comprises rotating the sample collection device to the second position such that the first end extends away from the cartridge; and bringing the first end into contact with the sample, whereby capillary action draws the sample into the channel and to the barrier.

26. A method as disclosed in embodiment 25, wherein the step of bringing the first end into contact with the sample comprises bringing the first end into contact with a drop of blood on an animal.

27. A method as disclosed in embodiment 25, wherein the rotation from the second position to the first position is approximately 180 degrees.

28. A method as disclosed in embodiment 22, wherein the step of rotating the sample collection device to position the first or second end into contact with a sample further comprises rotating the sample collection device to the third position.

29. A method as disclosed in embodiment 28, wherein the step of bringing the second end into contact with the sample comprises bringing the second end into contact with a syringe containing blood from an animal.

30. A method as disclosed in embodiment 29, wherein the rotation from the third position to the first position is approximately 90 degrees.

31. A method as disclosed in embodiment 22, wherein the sample is an aqueous fluid sample.

32. A method as disclosed in embodiment 31, wherein the sample is whole blood, serum, plasma or urine.

33. A method as disclosed in embodiment 29, wherein the animal is a mammal.

34. A method as disclosed in embodiment 26 wherein the animal is a mammal.

35. A method as disclosed in embodiment 33, wherein the mammal is a human.

36. A method as disclosed in embodiment 34, wherein the mammal is a human.

37. A method of performing an assay on a liquid sample for the presence or concentration of one or more analyte(s) or control(s), on the assay device according to embodiment 22, comprising: rotating the sample collection device to a second position to position the first end into contact with the sample, or rotating the sample collection device into a third position to position the sample collection well into contact with the sample; collecting the sample into the sample collection device; rotating the sample collection device to the first position to position the first end into position with the assay device; and applying air pressure to the air vent to force the sample into contact with a sample addition zone of the assay device; moving the sample by capillary action through a fluid flow path into a reagent zone where it dissolves one or more reagents; flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analytes or controls.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

What is claimed is:

1. A method for collecting a sample comprising:
providing a working element comprising:
a sample collection device for a fluid sample, the device comprising:
a substantially disk-shaped body having a periphery;
a capillary channel extending through the body and bounded by the periphery, having a first end and a second end, wherein the first end is adapted to draw the fluid into the channel by capillary action;
a sample collection well located in the vicinity of the second end and in fluid communication with the capillary channel; and
an axis of rotation extending through the center of the disk and which is substantially perpendicular to the major surface of the disk-shaped body; and
a cartridge having a housing comprising an air vent in fluid communication with the capillary channel when the disk is rotated in a first position, and containing a sample manipulation device, wherein the sample collection device is rotatably positioned within the cartridge and at least a portion of the side and top surface of the disk are exposed for application of sample;
rotating the sample collection device to a second position to position the first end into contact with a sample, or rotating the sample collection device into a third position to position the sample collection well into contact with a sample;
collecting the sample into the sample collection device;
rotating the sample collection device to the first position to position the first end into position with the sample manipulation device; and
applying air pressure to the air vent to force the sample into the sample manipulation device.

2. A method as claimed in claim 1, wherein the air vent is located in the vicinity of and in fluid communication with the second end of the capillary channel when the disk is rotated in a first position.

3. A method as claimed in claim 1, wherein the sample manipulation device includes a pre-manipulation portion.

4. A method as claimed in claim 1, wherein the step of rotating the sample collection device to position the first or second end into contact with a sample further comprises rotating the sample collection device to the second position such that the first end extends away from the cartridge; and bringing the first end into contact with the sample, whereby capillary action draws the sample into the channel.

5. A method as claimed in claim 4, wherein the step of bringing the first end into contact with the sample comprises bringing the first end into contact with a drop of blood on an animal.

6. A method as claimed in claim 4, wherein the rotation from the second position to the first position is approximately 180 degrees.

7. A method as claimed in claim 1, wherein the step of rotating the sample collection device to position the first or second end into contact with a sample further comprises rotating the sample collection device to the third position.

8. A method as claimed in claim 7, wherein the step of bringing the second end into contact with the sample comprises bringing the second end into contact with a syringe containing blood from an animal.

9. A method as claimed in claim 8, wherein the rotation from the third position to the first position is approximately 90 degrees.

10. A method as claimed in claim 1, wherein the sample is an aqueous fluid sample.

11. A method as claimed in claim 10, wherein the sample is whole blood, serum, plasma or urine.

12. A method as claimed in claim 8, wherein the animal is a mammal.

13. A method as claimed in claim 5, wherein the animal is a mammal.

14. A method as claimed in claim 12, wherein the mammal is a human.

15. A method as claimed in claim 13, wherein the mammal is a human.

16. A method of performing an assay on a liquid sample for the presence or concentration of one or more analyte(s) or control(s), on the assay device according to claim 1, comprising:
   rotating the sample collection device to a second position to position the first end into contact with the sample, or rotating the sample collection device into a third position to position the sample collection well into contact with the sample;
   collecting the sample into the sample collection device;
   rotating the sample collection device to the first position to position the first end into position with the assay device; and
   applying air pressure to the air vent to force the sample into contact with a sample addition zone of the assay device;
   moving the sample by capillary action through a fluid flow path into a reagent zone where it dissolves one or more reagents;
   flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and
   reading the signal(s) that are produced in the detection zones to determine the presence or concentration of the analytes or controls.

* * * * *